United States Patent [19]
Roulier et al.

[11] Patent Number: 5,763,500
[45] Date of Patent: Jun. 9, 1998

[54] EXPANDED SOLID COMPOSITION WHOSE MATRIX COMPRISES A STARCH-BASED CELLULAR NETWORK AND WHICH CONTAINS SIZE-GRADED SPHEROIDAL POLYAMIDE PARTICLES AND ITS USES IN TOPICAL APPLICATION

[75] Inventors: Véronique Roulier, Paris; Myriam Mellul, L'Hay-les-Roses; Gérard Gabin, Paris, all of France; Katrin Holz, Lausanne, Switzerland

[73] Assignee: L'Oreal, Paris, France

[21] Appl. No.: 654,606

[22] Filed: May 29, 1996

[30] Foreign Application Priority Data

May 29, 1995 [FR] France ................... 95 06322

[51] Int. Cl.⁶ ........................................... C08J 9/04
[52] U.S. Cl. ............... 521/84.1; 521/109.1; 521/149; 521/916; 424/69; 424/70.1; 424/78.02; 424/78.35
[58] Field of Search ............... 521/84.1, 109.1, 521/149, 916; 424/69, 70.1, 78.02, 78.35

[56] References Cited

U.S. PATENT DOCUMENTS

| | | |
|---|---|---|
| 4,831,051 | 5/1989 | Bourgery et al. |
| 5,506,277 | 4/1996 | Griesbach, III ............... 521/84.1 |

FOREIGN PATENT DOCUMENTS

| | | |
|---|---|---|
| 0 544 349 | 6/1993 | European Pat. Off. |
| 2 555 441 | 5/1985 | France |
| 61-207320 | 9/1986 | Japan |
| WO 92/08759 | 5/1992 | WIPO |

*Primary Examiner*—John M. Cooney, Jr.
*Attorney, Agent, or Firm*—Finnegan, Henderson, Farabow, Garrett & Dunner, L.L.P.

[57] ABSTRACT

The present application relates to expanded solid compositions whose matrix comprises a cellular network formed from a starch-rich product and contains size-graded spheroidal polyamide particles. These compositions constitute new dosage forms for cosmetic or dermatological use. These compositions take either the form of expanded cylinders, pellets, leaves or flakes, or the form of powder. When reduced to the powder state, these compositions may also be used as pulverulent phase in make-up compositions, in particular make-up powders. They may be stored in the dry state and capable of being partially rehydrated after immersion in water to reconstitute make-up removal or gentle exfoliating compositions for the skin, body, face and/or neck.

21 Claims, No Drawings

EXPANDED SOLID COMPOSITION WHOSE MATRIX COMPRISES A STARCH-BASED CELLULAR NETWORK AND WHICH CONTAINS SIZE-GRADED SPHEROIDAL POLYAMIDE PARTICLES AND ITS USES IN TOPICAL APPLICATION

The present invention relates to expanded solid compositions whose matrix comprises of a cellular network formed from a starch-rich product and contains size-graded spheroidal polyamide particles, as well as to their uses in topical application.

Expanded products based on starch and on edible ingredients, obtained by extrusion in one or more single- or twin-screw extruders, in particular aperitif snacks, crisps, cornflakes, breakfast cereals and biscuits, are known in the food industry.

The inventors have discovered, surprisingly, new dosage forms for cosmetic or dermatological use, in the form of an expanded solid composition whose matrix comprises a cellular network formed from a starch-rich product and contains size-graded spheroidal polyamide particles, as well as to their uses in topical application.

The inventors have also discovered, unexpectedly, that the introduction of size-graded spheroidal polyamide particles into a matrix comprising a starch-based cellular network and obtained by extrusion enabled expanded products of very great lightness and capable of attaining large expansion volumes to be obtained. The inventors found that, when reduced to powder, such products constituted make-up fillers of great softness and great lightness and displayed good disintegration properties.

The compositions of the invention, due to their novel starch-based cellular structure, can constitute new solid dosage forms for make-up in the form of expanded cylinders, pellets, leaves or flakes applied directly to the skin or the face, or can be reduced to powder and used in a traditional manner as make-up powder.

They can also take the form of powder for care and/or hygiene, applied directly to the skin, scalp or hair, for example dry shampoos or loose powders for body care. They can also take either the form of powder or the form of expanded cylinders, pellets, leaves or flakes, stored in the dry state and capable of being partially rehydrated after immersion in an aqueous medium to reconstitute make-up removal products or formulations for the gentle exfoliation of the skin, body, face and/or neck.

The common exfoliating products, also known as "scrubs", contain either fatty particles which melt and are difficult to remove from the skin by massage, or insoluble particles consisting of hard fillers which generally possess the drawback of being too abrasive, of being too irritating, of rubbing the skin without melting and of remaining on the skin.

The compositions according to the invention, due to their expanded starch-based cellular structure and the presence of size-graded spheroidal polyamide particles, can form directly, after immersion in water, suspensions of light, expanded particles which exert a substantially gentle exfoliating action and which can be readily removed by massage.

When reduced to the powder state, the compositions according to the invention may also be used as pulverulent phase in the manufacture of make-up products, and especially compacted powders, and can lead to lighter powders having a very gentle and non-fatty feel.

The compositions according to the invention are expanded solid compositions whose matrix comprises a cellular network formed from a starch-rich product and contains size-graded spheroidal polyamide particles.

As a general rule, the polyamides used are listed under the CTFA name "nylon 12" or "nylon 6". The polyamide particles used in the invention may be those sold under the name ORGASOL by Atochem. The process for obtaining these particles is, for example, the one described in French Patent Application FR 2,619,385 or in European Patent Application EP 303,530, the disclosures of which are hereby incorporated by reference. These polyamide particles are, moreover, known, depending on their different physicochemical properties, under the name "polyamide 12" or "polyamide 6".

The particles used in the invention may also be those sold under the name SP500 by Kobo.

In the compositions according to the invention, the particles preferably have a density ranging from 1 g/cm$^3$ to 1.84 g/cm$^3$, and more preferably a density ranging from 1.0 g/cm$^3$ to 1.4 g/cm$^3$.

The particles of the invention are generally spherical and solid; they have average sizes preferably ranging from 5 pm to 50 pm, and more preferably ranging from 10 µm to 30 µm.

The polyamide particles are present in the compositions of the invention in concentrations preferably ranging from 20 to 80% by weight, and more preferably from 30 to 70% by weight, relative to the total weight of the composition.

The starch-rich products used in the compositions according to the invention are preferably chosen from cereal flours such as wheat flour, corn flour, rice flour, oatmeal and wheat-germ flour or potato flour; pure starches commonly used in foods, such as maize, potato, tapioca and oat starches, starches modified in respect of the amylose/amylopectin ratio, such as the product HYLON VII sold by Amylum; and starches modified by crosslinking or modified with a functional group, such as the crosslinked maize starch sold under the name RESISTAMYL E2 by Amylum, the weakly quaternized maize starch sold under the name MYPLUS W7 by Amylum, the potato starch sold under the name SUPRAMYL P 60 by Amylum or the hydroxypropylated maize starch sold under the name MERIGEL EF6 by Amylum.

The matrix comprising the starch-based cellular network formed from these starch-rich products is present in the compositions according to the invention in a proportion preferably ranging from 20 to 80% by weight, and more preferably from 30 to 70% by weight, relative to the total weight of the composition.

The compositions according to the invention possess a water content preferably not exceeding 5% by weight, and more preferably ranging from 1 to 2% by weight, relative to the weight of the composition.

The compositions according to the invention can contain, in addition, a fatty phase. This fatty phase can comprise oils and/or waxes of animal, vegetable, mineral or synthetic origin, alone or mixed.

Among oils which can be used, there may be mentioned mink oil, turtle oil, soya-bean oil, grape-pip oil, sesame oil, maize oil, rape oil, sunflower oil, cottonseed oil, avocado oil, olive oil, castor oil, jojoba oil, groundnut oil; hydrocarbon oils such as liquid paraffin, squalane, petroleum jelly; fatty esters such as isopropyl myristate, isopropyl palmitate, butyl stearate, hexyl laurate, isononyl isononate, 2-ethylhexyl palmitate, 2-hexyldecyl laurate, 2-octyidecyl palmitate, 2-octyldodecyl myristate or lactate, 2-diethylhexyl succinate, diisostearyl malate, glyceryl or diglyceryl triisostearate; silicone oils such as polymethylsiloxanes, polymethylphenyl-siloxanes, polysiloxanes modified with fatty acids, fatty alcohols or polyoxyalkylenes, fluorinated silicones, perfluorinated oils; higher fatty acids such as myristic acid, palmitic acid, stearic acid, behenic acid, oleic acid, linoleic acid, linolenic acid or isostearic acid; and higher fatty alcohols such as cetanol, stearyl alcohol or oleyl alcohol.

Among waxes which can be used, there may be mentioned beeswaxes, lanolin waxes and Chinese insect waxes; carnauba, candelilla and ouricury waxes, cork-fibre waxes, sugar-cane waxes, Japan waxes, hydrogenated jojoba waxes and hydrogenated oils such as hydrogenated sunflower oil, hydrogenated castor oil, hydrogenated coconut oil and hydrogenated lanolin; paraffins, microcrystalline waxes, montan waxes and ozokerites; polyethylene waxes, waxes obtained by Fischer-Tropsch synthesis, waxy copolymers as well as their esters, and silicone waxes such as polyalkoxy- and polyalkyl siloxanes.

The fatty phase is present in proportions preferably ranging from 0.5 to 5% by weight, and more preferably from 0.3 to 5% by weight, relative to the total weight of the composition.

The fatty phase can, in addition, comprise additives such as lipophilic cosmetic active agents and/or fat-soluble ingredients generally used in cosmetics, such as perfumes. Preferably, these additives may be present in an amount of 0–20% relative to the total weight of the fatty phase.

The compositions according to the invention can contain, in addition, pigments, preferably in an amount of 0–50% relative to the total weight of the final composition. These pigments may be chosen from inorganic pigments, organic pigments and pearlescent pigments.

Among inorganic pigments, there may be mentioned, for example, titanium dioxide (rutile or anatase), optionally surface-treated; black, yellow, red and brown iron oxides; manganese violet; ultramarine blue; chromium oxide, optionally hydrated; and ferric blue.

Among organic pigments, there may be mentioned, for example, the pigments D & C red, D & C orange, D & C yellow, carbon black and carmine-based lakes.

The pearlescent pigments may be chosen, in particular, from white pearlescent pigments such as titanium oxide-coated mica or bismuth oxychloride; and colored pearlescent pigments such as titanium-mica with iron oxides, titanium-mica with ferric blue or chromium oxide, titanium-mica with an organic pigment of the abovementioned type, as well as bismuth oxychloride-based pigments.

The compositions can also contain other inorganic or organic fillers customarily used in make-up products, such as, for example, talc, micas, kaolin, silica, zinc and titanium oxides, calcium carbonate, magnesium carbonate and magnesium hydrogen carbonate, powders of non-expanded synthetic polymers, and metal soaps derived from $C_8$–$C_{22}$ carboxylic acid. They are present in concentrations preferably ranging from 0 to 50% by weight relative to the weight of the composition.

The compositions according to the invention can also contain one or more nonionic, anionic, cationic or amphoteric surfactant(s) customarily used in cosmetics. The amount of surfactant agent used is preferably from 2 to 30% relative to the total weight of the composition.

The compositions according to the invention can also contain, in addition, water-soluble cosmetic active agents.

Among cosmetic active agents, there may be mentioned antioxidants or free-radical scavengers; hydrating or humectant agents such as glycerol and collagen; and UV screening agents such as benzophenone. These water-soluble active agents may be present in the final composition in an amount of preferably 0 to 20%, and more preferably 5 to 15%, by weight.

The present invention also relates to a process for preparing a composition as defined above, characterized in that the latter is preferably obtained from the starch-rich product, size-graded spheroidal polyamide particles and possible additional constituents such as are mentioned above in the presence of water, preferably by mixing, kneading and expansion in a twin-screw extruder.

The extruder preferably used for the process of the invention is chosen from twin-screw extruders such as the one described in French Patent Application FR 94/00756, the disclosure of which is hereby specifically incorporated by reference.

The starting materials are introduced at the entry of the twin-screw extruder into the feeding zone at room temperature, preferably at approximately 20° C., are then conveyed to the transport zone, preferably at a temperature of approximately 50° C., and are then kneaded and compressed in various zones of the extruder which are maintained at a temperature preferably ranging from 100 to 160° C.; the mass obtained is transported to the exit of the extruder and extruded through a die to undergo an expansion thereat.

During the mixing phase, the starch-rich product gelatinizes and forms, after extrusion, a cellular network constituting the matrix of the final expanded products. The polyamide particles partially melt and create an expanded matrix with the flour.

Another subject of the invention consists of new cosmetic or dermatological compositions, characterized in that they comprise an expanded solid composition as defined above.

These compositions can take the form of expanded cylinders, pellets or flakes, or can alternatively be reduced to the powder state. They may be stored in the dry state and capable of being partially rehydrated after immersion in water to form directly a liquid or semi-liquid aqueous suspension of expanded particles.

These compositions can be make-up products. They may be applied to the face either directly or by means of a make-up tool such a brush, a powder puff or an applicator pad.

The compositions according to the invention can be products for the care and/or hygiene of the skin, mucosae, scalp or hair.

They can take the form of powder and be applied directly to the skin, scalp or hair, such as, for example, a dry shampoo or a loose powder for body care.

These compositions can also take the form of powder or alternatively of expanded cylinders, pellets or flakes, stored in the dry state and capable of being partially rehydrated after immersion in water to form a make-up removal composition or a gentle exfoliating composition for the skin, body, face and/or neck.

Naturally, a person skilled in the art will make sure to choose one or more possible additional compounds and/or the amounts thereof in such a way that the advantageous properties intrinsically associated with the composition according to the invention are not, or are not substantially, impaired by the addition(s) envisaged.

The examples which follow serve to illustrate the invention without, however, limiting its scope.

EXAMPLES

Example 1—Gentle exfoliant in the form of powder to be rehydrated

The final product had the following formulation:

| | |
|---|---|
| Wheat flour | 35.0% by weight |
| Size-graded spheroidal polyamide particles sold by Atochem under the name ORGASOL | 50.0% by weight |
| Silica sold by Maprecos under the name SB700 | 15.0% by weight |

PROCEDURE:

The pellets were obtained by extrusion in a twin-screw extruder. The starting materials were introduced at the entry of the extruder at a temperature of 30° C. They were then conveyed to the transport zone at a temperature of 50° C., and were thereafter kneaded and compressed in various zones of the extruder which were maintained at 120° C. The mass thus kneaded and compressed was transported to the exit of the extruder and extruded through a die 5 mm in diameter. The speed of rotation of the screws was 500 rpm. The cylinders obtained at the exit of the die were reduced to the powder state by means of a standard toothed roll crusher placed at the exit of the extruder. The product in powder form formed a gentle exfoliating composition after rehydration in water at the time of use.

Example 2—Foaming make-up remover in the form of pellets to be rehydrated

The final product had the following formula:

| | |
|---|---|
| Wheat flour | 40.0% by weight |
| Size-graded spheroidal polyamide particles sold by Atochem under the name ORGASOL | 40.0% by weight |
| Talc | 10.0% by weight |
| Sodium lauryl ether sulphate | 10.0% by weight |

PROCEDURE:

The pellets were obtained by extrusion in a twin-screw extruder. The starting materials were introduced at the entry of the extruder at a temperature of 30° C. They were then conveyed to the transport zone at a temperature of 50° C., and were thereafter kneaded and compressed in various zones of the extruder which were maintained at 120° C. The mass thus kneaded and compressed was transported to the exit of the extruder and extruded through a die 5 mm in diameter. The speed of rotation of the screws was 500 rpm. The cylinders obtained at the exit of the die were reduced in the form of pellets 3 mm in diameter by means of a granulator knife at the exit of the extruder. The product in powder form formed a make-up removal composition after rehydration in water at the time of use.

COMPARATIVE EXAMPLE

Expanded cylinders having the following formulation were prepared:

| Formulation A: | |
|---|---|
| Wheat flour | 80.0% by weight |
| Talc | 10.0% by weight |
| Sodium lauryl ether sulphate | 10.0% by weight |

Expanded cylinders according to the invention having the following formulation were also prepared:

| Formulation B: | |
|---|---|
| Wheat flour | 40.0% by weight |
| Size-graded spheroidal polyamide particles sold by Atochem under the name ORGASOL | 40.0% by weight |
| Talc | 10.0% by weight |
| Sodium lauryl ether sulphate | 10.0% by weight |

The expanded cylinders of formulation A or B were manufactured according to the same procedure as Example 2; the diameter of the die at the exit of the extruder was 5 mm.

The average diameter of the section of a cylinder of formulation A was 8–10 mm, while that of an expanded cylinder of formulation B was 14–16 mm. Hence, the expanded cylinders according to the invention had a substantially higher degree of expansion than that of cylinders not containing polyamide particles.

What is claimed is:

1. An expanded solid cosmetic or dermatological composition with a matrix which comprises a cellular network formed from a starch-rich product and which contains size-graded spheroidal polyamide particles, wherein said composition is in the form of a make-up product, a product for the care and/or hygiene of the skin, mucosae, scalp or hair.

2. A composition according to claim 1, wherein said polyamide particles have a density ranging from 1 $g/cm^3$ to 1.84 $g/cm^3$.

3. A composition according to claim 2, wherein said polyamide particles have a density ranging from 1 $g/cm^3$ to 1.4 $g/cm^3$.

4. A composition according to claim 1, wherein said polyamide particles have a particle size ranging from 5 µm to 50 µm.

5. A composition according to claim 1, wherein said composition contains from 20 to 80% by weight of said polyamide particles relative to the total weight of the composition.

6. A composition according to claim 1, wherein said starch-rich product is selected from cereal flours; potato flours; pure starches; starches modified in respect of the amylose/amylopectin ratio; crosslinked starches;

and starches modified with a functional group.

7. A composition according to claim 1, wherein said matrix comprising of a starch-based cellular network represents from 20 to 80% by weight of the total weight of the composition.

8. A composition according to claim 1, wherein said composition further comprises water present in an amount not exceeding 5% by weight relative to the total weight of the composition.

9. A composition according to claim 8, wherein water is present in an amount of from 1 to 2% by weight relative to the total weight of the composition.

10. A composition according to claim 1, wherein said composition further contains a fatty phase.

11. A composition according to claim 10, wherein said fatty phase comprises 0.5 to 5% by weight of said composition.

12. A composition according to claim 10, wherein said fatty phase comprises oils of animal, vegetable, mineral or synthetic origin, waxes of animal, vegetable, mineral or synthetic origin, or a mixture thereof.

13. A composition according to claim 1, wherein said composition further contains adjuvants selected from pigments, inorganic or organic fillers, surfactants, fat-soluble active agents, fat-soluble additives customarily used in cosmetics, antioxidants, free-radical scavengers, hydrating agents, humectants and sunscreen agents.

14. A process for preparing the composition as defined in claim 1, wherein the starting materials for said process include said starch-rich product, said size-graded spheroidal polyamide particles and water, said process comprising:

mixing said starting materials together to form a mixture in a twin- screw extruder;

kneading said mixture in said extruder; and expanding and extruding said kneaded mixture in said extruder.

15. A process according to claim 14, comprising:

introducing said starting materials to the extruder at room temperature;

conveying said starting materials to the transport zone at a temperature of approximately 50° C.;

kneading and compressing said materials in various zones of the extruder, said zones being maintained at a temperature ranging from 100 to 160° C., to obtain a kneaded and compressed mass;

transporting the mass obtained to the exit of the extruder; and extruding said mass through a die to undergo an expansion.

16. A process for preparing the composition as defined in claim 1, wherein the starting materials for said process include said starch-rich product, said size-graded spheroidal polyamide particles and water, said process comprising: mixing said starting materials together to form a mixture and processing said mixture to obtain said expanded solid composition.

17. An expanded solid cosmetic or dermatological composition with a matrix which comprises a cellular network formed from a starch-rich product and which contains size-graded spheroidal polyamide particles, wherein said composition can be partially rehydrated after immersion in water and is capable of reconstituting a suspension of expanded particles.

18. A composition according to claim 17, wherein said composition is an exfoliating product for the skin, body, face and/or neck, or a make-up removal product.

19. An expanded solid composition with a matrix which comprises a cellular network formed from a starch-rich product and which contains size-graded spheroidal polyamide particles, wherein said composition is in the form of an expanded cylinder, pellet, leaf or flake, or is reduced to a powder state.

20. A make-up product comprising an expanded solid composition as defined in claim 18.

21. A product for the care and/or hygiene of the skin, mucosae, scalp or hair comprising an expanded solid composition as defined in claim 18.

* * * * *

UNITED STATES PATENT AND TRADEMARK OFFICE
CERTIFICATE OF CORRECTION

PATENT NO. : 5,763,500
DATED : June 9, 1998
INVENTOR(S) : Roulier et al.

It is certified that error appears in the above-identified patent and that said Letters Patent is hereby corrected as shown below:

In Claim 1, column 6, line 23, "particles." should read --particles,--.

In claim 1, column 6, line 24, "product." should read --product,--.

In claim 14, column 7, line 9, "twin- screw" should read --twin-screw--.

Signed and Sealed this

Eighteenth Day of August, 1998

Attest:

BRUCE LEHMAN

Attesting Officer

Commissioner of Patents and Trademarks